United States Patent
Lopez et al.

(10) Patent No.: US 11,944,956 B2
(45) Date of Patent: Apr. 2, 2024

(54) ROOM TEMPERATURE LIQUID METAL CATALYSTS AND METHODS OF USE

(71) Applicant: THE REGENTS OF THE UNIVERSITY OF CALIFORNIA, Oakland, CA (US)

(72) Inventors: Isai Lopez, Santa Cruz, CA (US); Gabriella Amberchan, Santa Cruz, CA (US); Bakthan Singaram, Santa Cruz, CA (US); Scott Oliver, Santa Cruz, CA (US); Jeremy Barnett, Santa Cruz, CA (US); Beatriz Ehlke Santi Grott, Santa Cruz, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 269 days.

(21) Appl. No.: 17/607,424

(22) PCT Filed: Apr. 30, 2020

(86) PCT No.: PCT/US2020/030725
§ 371 (c)(1),
(2) Date: Oct. 29, 2021

(87) PCT Pub. No.: WO2020/223489
PCT Pub. Date: Nov. 5, 2020

(65) Prior Publication Data
US 2022/0219144 A1    Jul. 14, 2022

Related U.S. Application Data

(60) Provisional application No. 62/842,420, filed on May 2, 2019.

(51) Int. Cl.
| | | |
|---|---|---|
| B01J 23/08 | (2006.01) | |
| B01J 35/02 | (2006.01) | |
| B01J 35/12 | (2006.01) | |
| B01J 37/04 | (2006.01) | |
| C01B 3/08 | (2006.01) | |
| C07C 5/03 | (2006.01) | |

(52) U.S. Cl.
CPC ............ *B01J 23/08* (2013.01); *B01J 35/023* (2013.01); *B01J 35/12* (2013.01); *B01J 37/04* (2013.01); *C01B 3/08* (2013.01); *C07C 5/03* (2013.01); *C07C 2521/04* (2013.01); *C07C 2523/08* (2013.01)

(58) Field of Classification Search
None
See application file for complete search history.

(56) References Cited

U.S. PATENT DOCUMENTS

| | | | |
|---|---|---|---|
| 4,224,087 A * | 9/1980 | Tachikawa ......... | H10N 60/0184 29/599 |
| 4,358,291 A | 11/1982 | Cuomo et al. | |
| 4,385,942 A * | 5/1983 | Tachikawa ......... | H10N 60/0184 29/599 |
| 2008/0056986 A1 | 3/2008 | Woodall et al. | |
| 2008/0063597 A1 | 3/2008 | Woodall et al. | |
| 2009/0242395 A1 * | 10/2009 | Takagi ............... | C23C 14/3414 427/383.1 |
| 2013/0187170 A1 * | 7/2013 | Fukuyama ............... | C30B 9/10 117/64 |
| 2014/0196899 A1 * | 7/2014 | Jordan ................... | C22C 32/00 427/314 |
| 2022/0016611 A1 * | 1/2022 | Liu ....................... | C01B 37/02 |
| 2022/0380869 A1 * | 12/2022 | Guo ....................... | C22C 21/04 |
| 2023/0366284 A1 * | 11/2023 | Alghamdi ............... | E21B 31/16 |

OTHER PUBLICATIONS

Parmuzina et al., "Activation of Aluminum Metal to Evolve Hydrogen from Water", International Journal of Hydrogen Energy, 2008, vol. 33, pp. 3073-3076.
Ziebarth, et al., "Liquid Phase-Enabled Reaction of Al—Ga and Al—Ga—In—Sn Alloys with Water", International Journal of Hydrogen Energy, 2001, vol. 36., pp. 5271-5279.
International Search Report and Written Opinion dated Sep. 11, 2020 issued in corresponding PCT Appln. No. PCT/US2020/030725.
Jackson Ross Thomas, "Continuous Generation of Hydrogen and Aluminum Hydroxide from Hydrolysis Using an Active Aluminum-Gallium Molten Alloy", Thesis, B.S. (University of California, Davis) submitted 2015.

* cited by examiner

*Primary Examiner* — Tam M Nguyen
(74) *Attorney, Agent, or Firm* — Carter, DeLuca & Farrell LLP (57) ABSTRACT

A catalyst composition includes a liquid metal alloy having a melting point from about 20° C. to about 25° C., the liquid metal alloy including a primary metal and a secondary metal, the primary metal being aluminum and the secondary metal is selected from the group consisting of gallium, indium, and bismuth.

6 Claims, 6 Drawing Sheets

ROOM TEMPERATURE LIQUID METAL CATALYSTS AND METHODS OF USE

CROSS REFERENCE TO RELATED APPLICATIONS

The present application is a National Stage Application under 35 U.S.C. § 371(a) of PCT/US2020/030725, filed Apr. 30, 2020, which claims the benefit of and priority to U.S. Patent Provisional Application No. filed 62/842,420 filed on May 2, 2019. The entire disclosures of the foregoing applications are incorporated by reference herein.

BACKGROUND

The generation of sustainable, renewable energy with new or existing materials has long been sought, even before the correlation between fossil fuel emissions and climate change. Hydrogen fuel is an appealing option because it has a substantial energy density and the main byproduct of its combustion is water vapor, leading to its designation as a "clean fuel". Water splitting via hydrogen evolution reactions (HER) can be performed via electrocatalysis, photocatalysis, and electrolysis. These methods, however, require expensive catalysts (e.g. platinum-on-carbon (Pt/C), ruthenium-on-carbon (Ru/C), iridium-on-carbon (Ir/C) catalysts) and/or an applied potential and thus, are not feasible as a continuous, affordable source.

HER are an important process in electrochemical energy conversion and storage. In particular, HER plays a significant role in electrochemical water splitting for clean and sustainable hydrogen energy. Therefore, finding a way to generate hydrogen from water in an efficient, economical manner is of great societal importance. Accordingly, there is a need for new methods of generating hydrogen gas in an economically viable manner.

SUMMARY

Activated aluminum (Al) upon contact with water rapidly generates hydrogen gas ($H_2$). However, this reaction passivates the Al and prevents further oxidation and continued generation of hydrogen gas. To overcome the passivation of aluminum, the present disclosure provides low temperature liquid metal catalysts, which are aluminum alloys of two or more constituent metals (one of which is aluminum). The alloys are low temperature (e.g., room temperature) eutectic alloys, which react with water at room temperature. As used herein the term "eutectic alloy" denotes a homogenous alloy of two or more metals having a lower melting point than the melting point of any of the constituent metal of the alloy.

Disclosed herein are compositions that include aluminum, e.g., from aluminum foil, and methods for generating hydrogen on-demand at room temperature in liquid gallium (Ga). The Ga—Al alloy according to the present disclosure is stable under cyclohexane for at least several months and may be stored for later user when and where hydrogen is needed. Several examples of HERs are also disclosed herein. The hydrogen synthesis and water splitting reaction is performed at room temperature, under atmospheric pressure, neutral pH, with no catalytic electrodes or an applied potential. Any source of water including wastewater or ocean water may be used. Notably, hydrogen may be generated from ocean water with no detectable chlorine gas produced. Gallium may be fully recovered after the HER and therefore reused indefinitely. Aluminum nanoparticles in the gallium are responsible for HER, as predicted by theoretical calculations. Aluminum oxide is another byproduct and has practical uses of its own and may be used to regenerate elemental aluminum.

Aluminum is economically viable as a raw material for producing hydrogen because it is in high abundance (e.g., approximately 8 wt. % in the earth's crust). About 1 g of Aluminum is capable of producing about 1.24 L of hydrogen while generating aluminum oxide according to equation (I)

$$2Al + 3H'O \rightarrow Al'O + 3H' \qquad (I)$$

To access aluminum's potential, however, a passivating aluminum oxide layer, which forms on the surface of aluminum when it is in contact with air, needs to be removed. The layer may be removed using a variety of methods, such as mechanical manipulation, exposure to very high or low pH, or room temperature liquid metals. One such method is ball milling, which may be used to synthesize a powder from two or more materials. Those materials are subjected to a pressurized environment for extended periods of time to achieve a fine particle structure. The fine particle morphology allows for more surface area but there is greater susceptibility for the oxide coating to return. The powders must therefore be kept under an inert environment such as an argon-purged container. Concentrated acidic or alkaline solutions may also be used to remove the oxide layer but the reagents are highly corrosive and costly.

A room temperature liquid metal mixed with aluminum creates a eutectic system that simultaneously prevents the passivation layer from forming and liquifies the aluminum, allowing for efficient production of $H_2$. Woodall's discovery in 1968 that aluminum dissolved in gallium can split water opened the possibility that aluminum could be a viable hydrogen production material. Further research expanded into ternary, quaternary, and quinary alloys that involved mixing aluminum with gallium, indium (In), tin (Sn), and bismuth (Bi) in various ratios. The motivation for producing some of these alloys was to generate $H_2$ at less elevated temperature. The toxicity of tin, however, limits its industrial use.

Because the cost of gallium would be an economic barrier to widespread use, also disclosed herein is a method of recovering gallium after hydrogen generation and reusing it for multiple hydrogen generation cycles. While previous work focused on Al-rich alloys, it is shown herein that the Ga-rich alloys produce hydrogen in a far greater amount and at a much higher rate. The disclosed Ga—Al alloys are effective at splitting water under ambient conditions. Alloys were examined using a variety of characterization methods. Also disclosed are methods of using the alloys to produce hydrogen.

Previous reports of Ga—Al alloys used only Al-rich alloys to generate hydrogen. These required special milling techniques and higher temperatures to produce the alloys. The present disclosure provides Ga-rich alloys that are far more effective at producing hydrogen and can be made and used under ambient conditions. The gallium dissolves aluminum and removes the passivating oxide layer, which allows the pristine nanoaluminum surface to split water into hydrogen gas. Because the gallium selectively dissolves the aluminum, waste aluminum, such as from soda cans generates equivalent amounts of hydrogen as pure aluminum, without needing to expend energy into cleaning the surface.

Different types of water ranging from deionized (DI) water to ocean water were all compatible in generating stoichiometric amounts of hydrogen.

The alloys according to the present disclosure are soft grey color and appeared uniform. To better visualize the material, the alloy was fully characterized using electron microscopy techniques. Transmission electron microscopy (TEM) imaging showed nanoparticles of aluminum suspended in gallium. Powder X-ray diffraction (PXRD) and electron diffraction (ED) complemented those results by showing crystalline domains of aluminum and gallium in the material. Application of the alloy in a standard hydrogenation procedure demonstrated the simplicity of obtaining hydrogen without needing to pressurize the system. Following HER, the gallium can then be separated from the aluminum oxide, which is a byproduct of HER. The recovered gallium can be used to dissolve aluminum again without a detectable change in its ability to dissolve aluminum or in the resulting alloy's ability to generate hydrogen. In some embodiments, recovered gallium may be repeatedly used to form new alloys and regenerate hydrogen at least 10 times. In further embodiments, recovered gallium may be used at least 50 times. And in additional embodiments, recovered gallium may be used at least 100 times.

According to one embodiment of the present disclosure, a catalyst composition is disclosed. The catalyst composition includes gallium and aluminum at an atomic ratio from about 2:1 to about 5:1 of gallium to aluminum, wherein aluminum includes particles having an average size from about 5 nm to about 30 nm diameter dispersed in gallium.

According to one aspect of the above embodiment, the catalyst composition has a melting point from about 20° C. to about 25° C. The catalyst composition may include gallium and aluminum at an atomic ratio of from about 2.5:1 to about 4:1 of gallium to aluminum. The catalyst composition may include gallium and aluminum at an atomic ratio of from about 2.5:1 to about 3.5:1 of gallium to aluminum. The catalyst composition may be provided as a pellet of at least 0.1 g, at least 1 g, at least 10 g, at least 100 g, or at least 1000 g in mass may be stored under an alkane.

According to another aspect of the above embodiment, the method includes: combining gallium and aluminum at an atomic ratio from about 2:1 to about 5:1 of gallium to aluminum at a temperature from about 20° C. to about 30° C. to form a mixture of gallium and aluminum; and applying pressure to the mixture of gallium and aluminum until the aluminum has dissolved, thereby forming an alloy of gallium and aluminum.

According to one aspect of the above embodiment, the method further includes cooling the alloy of gallium and aluminum until it solidifies. The aluminum may be provided as a foil less than 0.5 mm in thickness. The aluminum may be provided as a foil less than 0.04 mm in thickness. The aluminum may be provided as particles less than 0.5 mm in diameter. The aluminum may be provided as particles less than 0.04 mm in diameter. The aluminum may be derived from a beverage can or food wrapper, wherein the beverage can, or food wrapper previously held a beverage or wrapped food.

According to another aspect of the above embodiment, the method further includes combining gallium and aluminum at an atomic ratio of from about 2.5:1 to about 4:1 of gallium to aluminum. The method may further include combining gallium and aluminum at an atomic ratio of from about 2.5:1 to about 3.5:1 of gallium to aluminum. Gallium used to form the alloy may be recovered and may have been previously combined with aluminum to form a previous alloy of gallium and aluminum and recovered from the previous alloy of gallium and aluminum. Gallium may be recoverable from the previous alloy of gallium and aluminum at least 10 times. Gallium may be recoverable from the previous alloy of gallium and aluminum at least 50 times. Gallium may be recoverable from the previous alloy of gallium and aluminum at least 100 times.

According to a further embodiment of the present disclosure, a method of making hydrogen gas is disclosed and includes contacting a catalyst composition including gallium and aluminum at an atomic ratio from about 2:1 to about 5:1 of gallium to aluminum with a hydrogen containing compound, thereby releasing hydrogen gas.

According to one aspect of the above embodiment, the catalyst composition may include gallium and aluminum at an atomic ratio of from about 2.5:1 to about 4:1 of gallium to aluminum. The catalyst composition may include gallium and aluminum at an atomic ratio of from about 2.5:1 to about 3.5:1 of gallium to aluminum. The catalyst composition may include gallium and aluminum at an atomic ratio from about 2:1 to about 5:1 of gallium to aluminum and aluminum includes particles having an average size from about 5 nm to about 30 nm diameter dispersed in gallium. The hydrogen containing compound may be water or an alcohol. The water may be deionized water, distilled water, well water, tap water, rainwater, wastewater, saltwater, ocean water, or combinations thereof. Alcohol may be methanol or ethanol.

According to one embodiment of the present disclosure, a method of hydrogenating an alkene is disclosed. The method includes contacting a first catalyst composition comprising gallium and aluminum at an atomic ratio from about 2:1 to about 5:1 of gallium to aluminum with water, thereby releasing hydrogen gas. The method also includes contacting the hydrogen gas with the alkene in the presence of a hydrogenation catalyst, thereby hydrogenating the alkene.

According to one aspect of the above embodiment, gallium and aluminum are present at an atomic ratio of from about 2.5:1 and 4:1 of gallium to aluminum. In another aspect, gallium and aluminum are present at an atomic ratio of from about 2.5:1 and 3.5:1 of gallium to aluminum. The first catalyst composition includes gallium and aluminum at an atomic ratio from about 2:1 to about 5:1 of gallium to aluminum. Aluminum includes particles having an average size from about 5 nm to about 30 nm diameter dispersed in gallium.

According to another aspect of the above embodiment, the releasing of the hydrogen gas is performed in a first container and the hydrogenation is performed in a second container. The first container and the second container are in fluid communication. The hydrogenation catalyst includes at least one of platinum or nickel.

According to another embodiment of the present disclosure, a catalyst composition is provided, which includes a liquid metal alloy having a melting point from about 20° C. to about 25° C. The liquid metal alloy includes a primary metal and a secondary metal, the primary metal being aluminum. The secondary metal may be one of gallium, indium, mercury, or bismuth.

According to one aspect of the above embodiment, the catalyst composition further includes a tertiary metal, wherein the tertiary metal is different from the secondary metal. The tertiary metal may be one of gallium, indium, mercury, or bismuth.

According to another embodiment of the present disclosure, a method for producing hydrogen is provided. The method includes contacting at least one hydrogen-containing compound to a catalyst composition to dehydrogenate the at least hydrogen-containing compound to form hydrogen. The catalyst composition includes a liquid metal alloy having a melting point from about 20° C. to about 25° C. The liquid metal alloy includes a primary metal and a secondary metal, the primary metal being aluminum. The secondary metal may be one of gallium, indium, or bismuth.

According to one aspect of the above embodiment, the method further includes: collecting the secondary metal; and synthesizing the liquid metal alloy from the collected secondary metal. The liquid metal alloy further includes a tertiary metal that is different from the secondary metal. The tertiary metal may be one of gallium, indium, mercury or bismuth.

According to another aspect of the above embodiment, the hydrogen-containing compound is water or an alcohol.

BRIEF DESCRIPTION OF DRAWINGS

Various embodiments of the present disclosure are described below with reference to the following figures.

DETAILED DESCRIPTION

The present disclosure provides a liquid metal catalyst, which may be an alloy of two or more metals, one of which may be aluminum. In embodiments, the liquid metal catalyst may be a binary alloy, which includes aluminum as a primary metal and a secondary metal, which may be one of gallium, bismuth, indium, and the like. The binary alloy of the liquid metal catalyst may include aluminum and the secondary metal at an atomic ratio from about 1:1 to about 1:4 of aluminum to the secondary metal. In further embodiments, the atomic ratio of aluminum to the secondary metal may be about 4:2.

In further embodiments, the liquid metal catalyst may be a ternary alloy of aluminum, a secondary metal and a tertiary metal. The secondary and tertiary metals are different and may be one of gallium, bismuth, indium, and the like. The ternary alloy of the liquid metal catalyst may include aluminum, the secondary metal, and the tertiary metal present at an approximate atomic ratio 1:1:1, 1:1:2, or 1:2:4, of aluminum, the secondary metal, and the tertiary metal.

The liquid metal catalyst may be formed by combining aluminum with a secondary metal and/or tertiary metal at the atomic ratios disclosed above. Aluminum may be dissolved in the secondary and/or tertiary metals by heating the constituent metals under inert atmosphere. In further embodiments, the constituent metals may be mixed without heating under inert atmosphere by folding and pressing the constituent metals together. The liquid metal catalyst may be formed as a droplet to minimize formation of an oxide layer, which inhibits hydrogen evolution, on the surface of the liquid metal catalyst.

The liquid metal catalyst may be a binary alloy of Ga and Al. Various atomic ratios of the Ga—Al alloys may be used to optimize the production of hydrogen. Ga—Al alloys having a higher Ga ratio produce larger amounts of hydrogen, compared to Al-rich alloys as shown in hydrogen production bar graphs of FIG. 7. In embodiments, gallium and aluminum may be present in the alloy at an atomic ratio from about 2:1 to about 5:1. In further embodiments, the ratio may be from about 2.5:1 to about 4:1 of gallium to aluminum. In additional embodiments, the ratio may be from 2.5:1 to about 3.5:1 of gallium to aluminum.

Ga:Al alloys have a melting point from about 20° C. to about 25° C. Ga:Al alloys may be formed by mechanically combining Ga and Al, such as by folding two metals at a temperature from about 20° C. to about 30° C. Folding the two metals results in production of aluminum nanoparticles, which may have an average particle size from about 5 nm to about 30 nm. Folding may include any application of pressure on the two metals that results in formation of the alloy.

Suitable aluminum may be obtained from any source such as foil, recyclable aluminum (e.g., cans, packaging, trays, etc.). Suitable aluminum foil may have a thickness of less than 0.5 mm. In embodiments, aluminum foil may have a thickness of less than 0.4 mm. Aluminum may also be provided as particles having an average diameter from about 0.01 mm to about 1 mm, and in embodiments may be about 0.5 mm and in further embodiments may be about 0.04 mm. The disclosed range has been found to be more effective mixing of the two metals.

Hydrogen generation occurs at the interface between aluminum and water, thus requiring a pristine aluminum surface. As noted above, aluminum does not generate hydrogen gas, as a passivating oxide layer prevents any reaction from occurring with water. According to the present disclosure, gallium may be used to dissolve aluminum, destroying any passivating aluminum oxide film and forming aluminum nanoparticles, enabling aluminum to split water and form aluminum hydroxide and hydrogen gas. The elemental distribution maps (FIGS. 8 and 9) show that aluminum is present in several areas on the gallium surface, indicating that aluminum nanoislands form within a sea of gallium by simple mechanical mixing.

Figure 3:
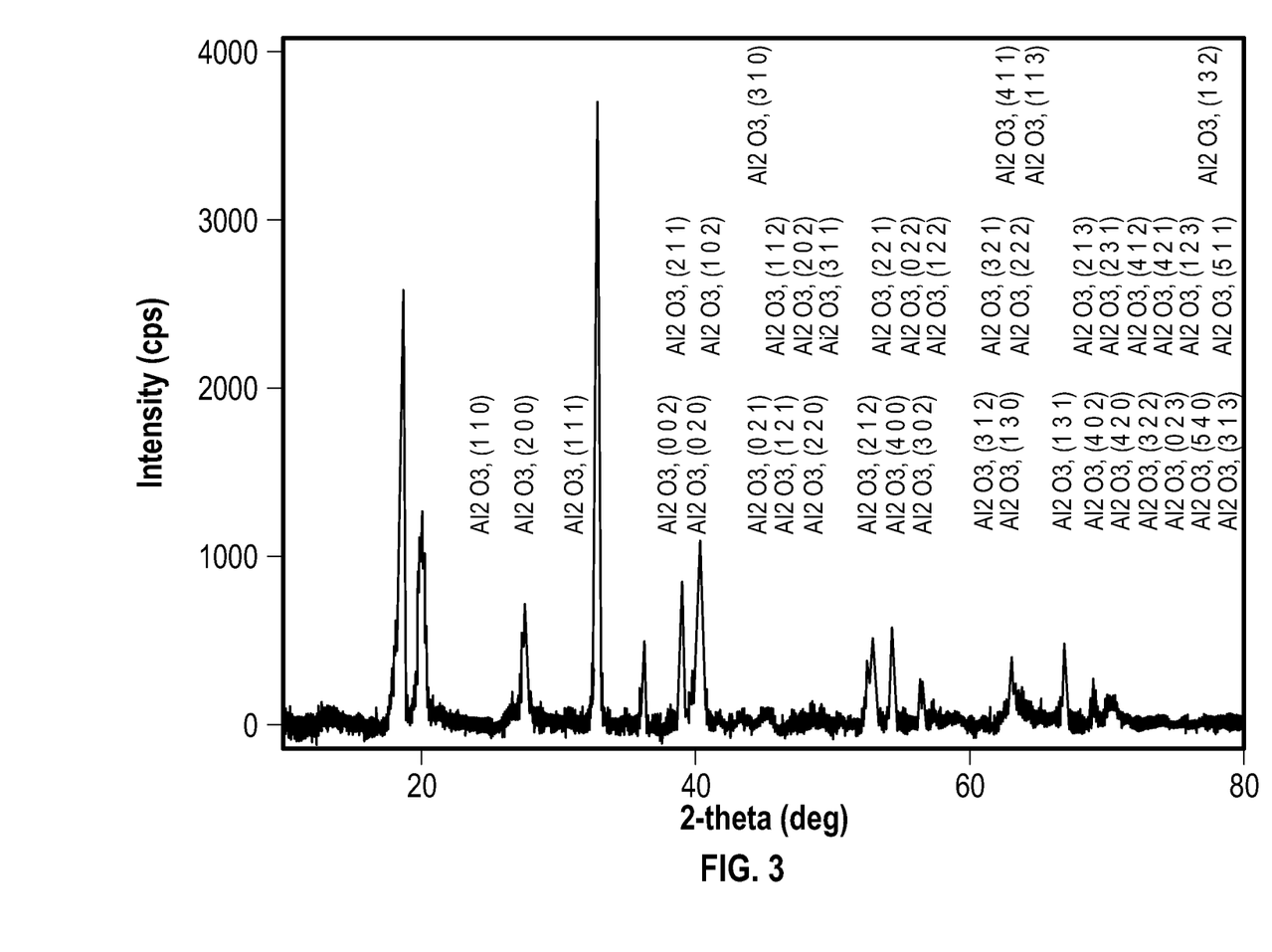
FIG. 3 is a powder X-ray diffraction (PXRD) spectrum of $Al_2O_3$ obtained as a byproduct
Figure 4:
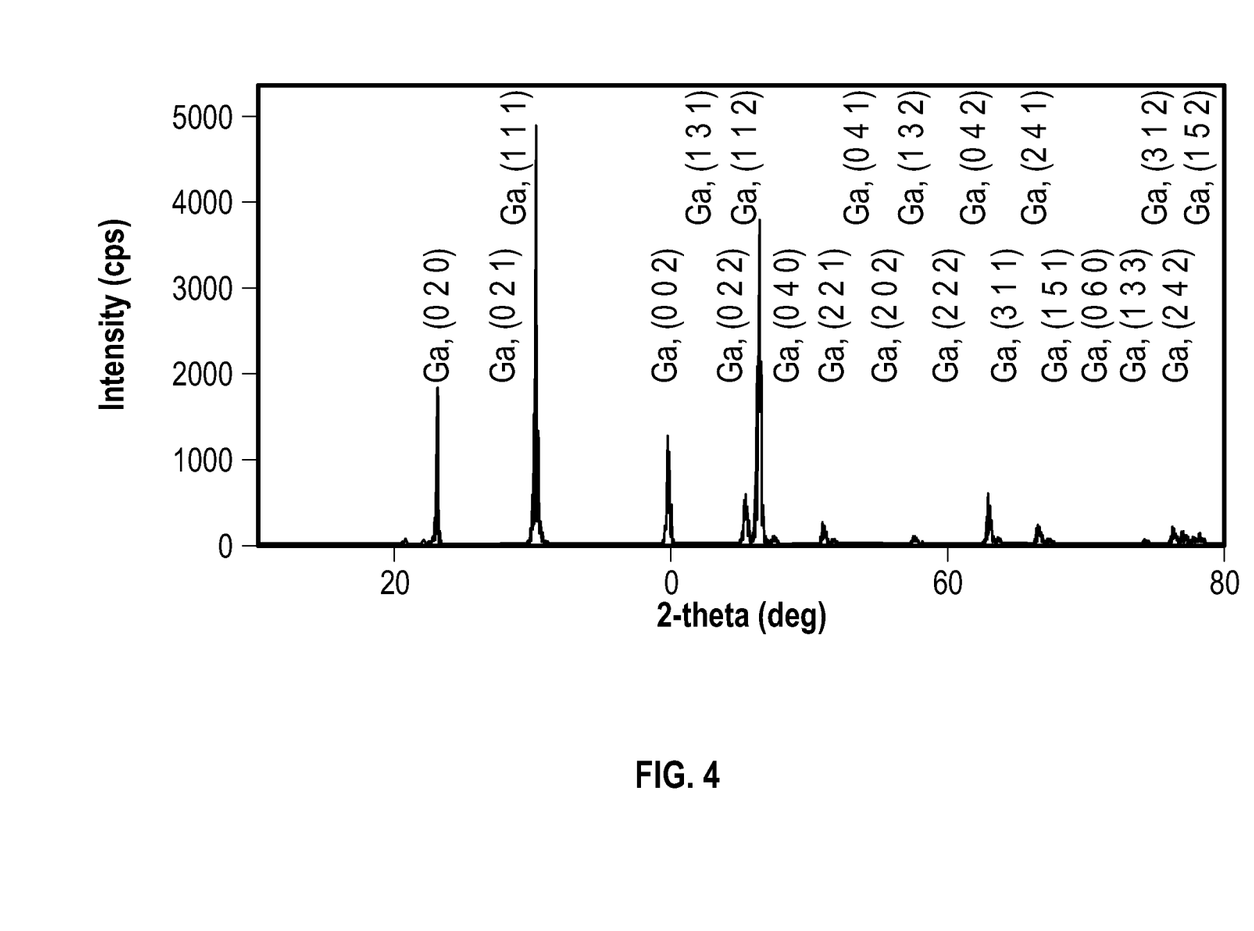
FIG. 4 is a PXRD spectrum of recovered gallium forming the liquid metal catalysts that were used in HER according to an embodiment of the present disclosure.
Figure 9:
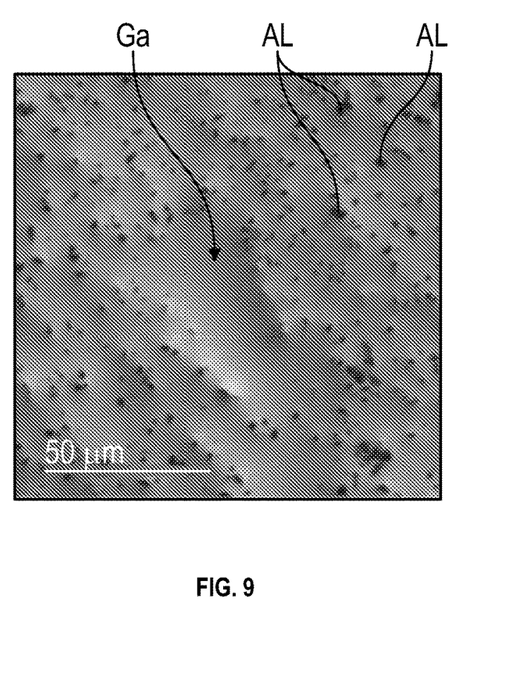
FIG. 9 is a scanning electron microscopy (SEM) image at 50 μm scale of Ga—Al alloy catalyst according to the present disclosure.
Figure 10:
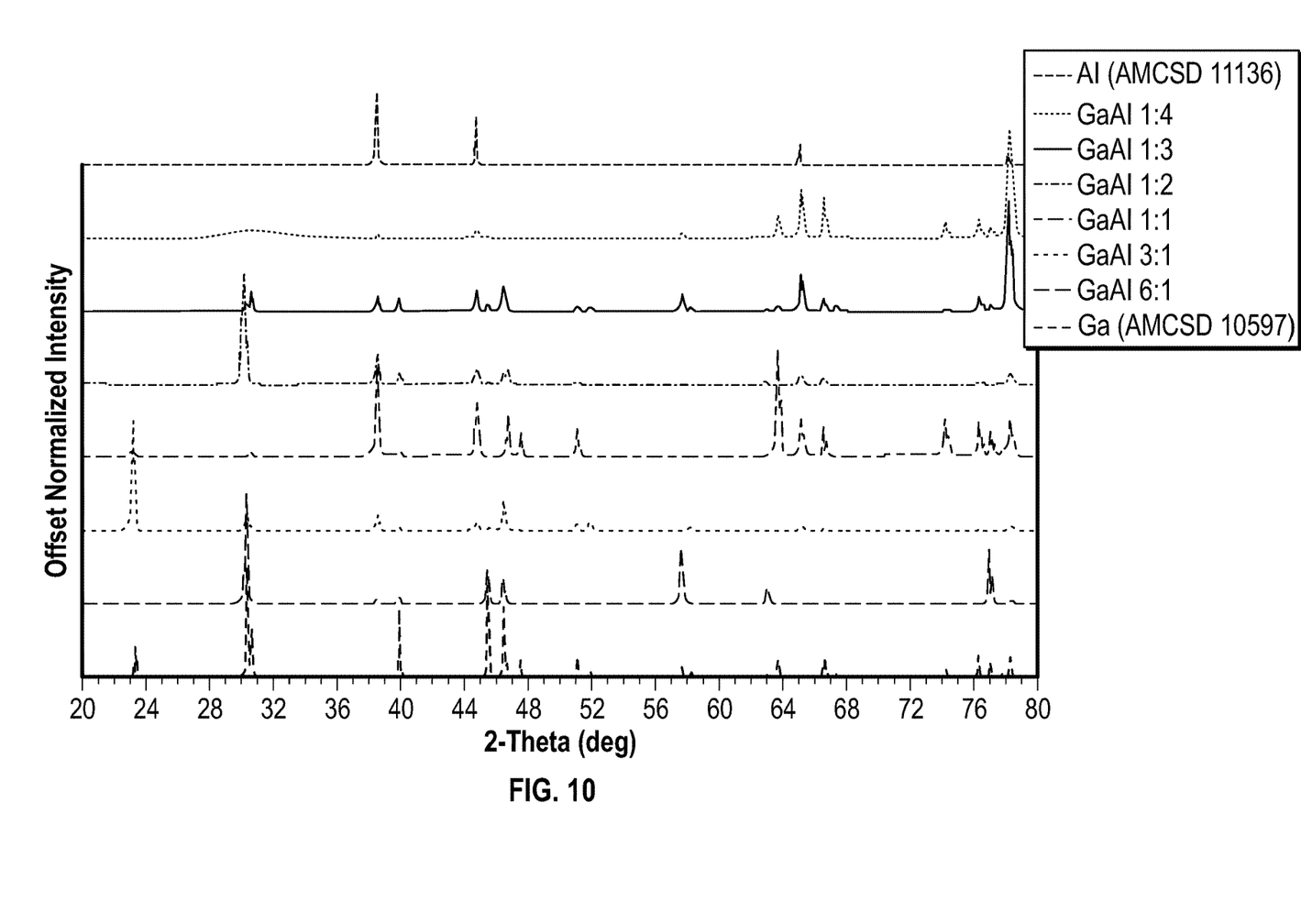
FIG. 10 shows PXRD spectra Ga—Al alloy catalysts and pure aluminum and gallium for comparison.

Each element maintains their individual crystal structures as seen in PXRD data (FIGS. 3, 4, and 10). Aluminum is present in the form of nanoparticles, as indicated by TEM data (FIGS. 8 and 9), which may have an average particle size from about 5 nm to about 30 nm, which in embodiments may be from about 10 nm to about 20 nm. At these nano-aluminum sites, a series of hydrogen bond exchanges occur to liberate hydrogen, a pathway similar to that of the theoretical Grotthuss mechanism. The byproduct $Al(OH)_3$/$Al_2O_3$ formed is porous and gets swept away to expose a new surface of Al on the nanoparticles again for further reaction. Density function theory calculations performed on 13-atoms clusters, such as $Al_{13}$, $GaAl_{12}$, and in-depth analysis of complementary Lewis acid/base pairs of these metal clusters reveal that doping of Ga in an $Al_{13}$ cluster reduces the transition state barrier for water splitting via simultaneous breaking of an O—H bond and Al—H bond.

The liquid metal catalysts according to the present disclosure have a melting point from about 20° C. to about 25° C., thereby acting as a room temperature liquid metal alloy. The use of liquid metal catalysts having a relatively low melting point enables continuous generation of hydrogen and oxidation of aluminum, which otherwise would be hindered by the formation of an oxide layer in solid phase aluminum.

In particular, the liquid metal catalysts according to the present disclosure may be used in HER. The rate of hydrogen generation from the HER according to present disclosure may be affected by the pH and temperature at which HER is carried out. Accordingly, the HER may be carried out at a pH from about 9 to about 13, in embodiments from about 10 to about 12. The HER may also be carried at a temperature from about 22° C. and 100° C., in embodiments from about 30° C. to about 80° C., and in further embodiments, from about 40° C. to about 60° C. HER may be carried with any suitable water, however, certain impurities present in the water may affect the rate of hydrogen generation. However, as shown, they have minimal effect on the process.

The method for hydrogen generation according to the present disclosure includes providing a liquid metal catalyst and exposing the catalyst to a hydrogen containing compound such as water or an aqueous solution. Exposure to the compound may be carried by placing the catalyst composition in a liquid container.

The hydrogen containing compound may be an aqueous alkaline medium, which may be prepared by dissolving an alkaline compound including alkali metal hydroxides such as lithium hydroxide, sodium hydroxide and potassium hydroxide, and tetraalkylammonium hydroxides such as tetramethylammonium hydroxide and tetraethylammonium hydroxide. Suitable solvents include pure water or water that is mixed with various water-miscible solvents including alcohols such as methyl and ethyl alcohols, dimethylformamide, dimethylacetamide, ethyleneglycol, diethyleneglycol and the like. The aqueous alkaline medium may include from about 1% by to about 30% by weight of the alkaline compound dissolved therein. The generated hydrogen may be collected or syphoned for later use. In further embodiments, the generated hydrogen may be used directly with any system and or apparatus that utilizes hydrogen as a source of fuel, such as a fuel cell.

The liquid metal catalyst alloys according to the present disclosure may be shaped into pellets of predetermined size and stored under cyclohexane and used when needed to prevent moisture from reducing effectiveness of the alloy. The pellets may be sized such that when contacting water, the pellets generate a predetermined amount of hydrogen. In embodiments, the pellets may be sized to produce 1 kg of hydrogen gas. Since the pellet size depends on the atom ratio of Ga:Al, which affects the hydrogen production, the pellet may be at least 0.1 g, at least 1 g, at least 10 g, at least 100 g, or at least 1000 g in mass The liquid metal catalyst is efficient in producing hydrogen during HER by producing from about 80% to about 90% of theoretical amount of hydrogen from water at about 25° C. During contact of the liquid metal catalyst with water, the resultant products include hydrogen gas ($H_2$), aluminum oxide ($Al_2O_3$), and regenerated secondary metal, which may be recovered at a yield of from about 80% to about 95% using any suitable solid separation technique such as filtration. The collected secondary and tertiary metals may then be recycled to form additional liquid metal catalyst compositions for subsequent use during HER.

In the liquid metal catalyst, aluminum activation is achieved by forming an alloy with one or more low melting point metals. Room temperature liquid metals are useful for their ability to create low melting point eutectic alloy. Since the liquid metal catalyst is a eutectic alloy having a melting point from about 20° C. to about 25° C., the liquid metal catalyst maintains its liquid phase under room temperature. This in turn allows HER to occur at temperatures near or at room temperature.

Figure 7:
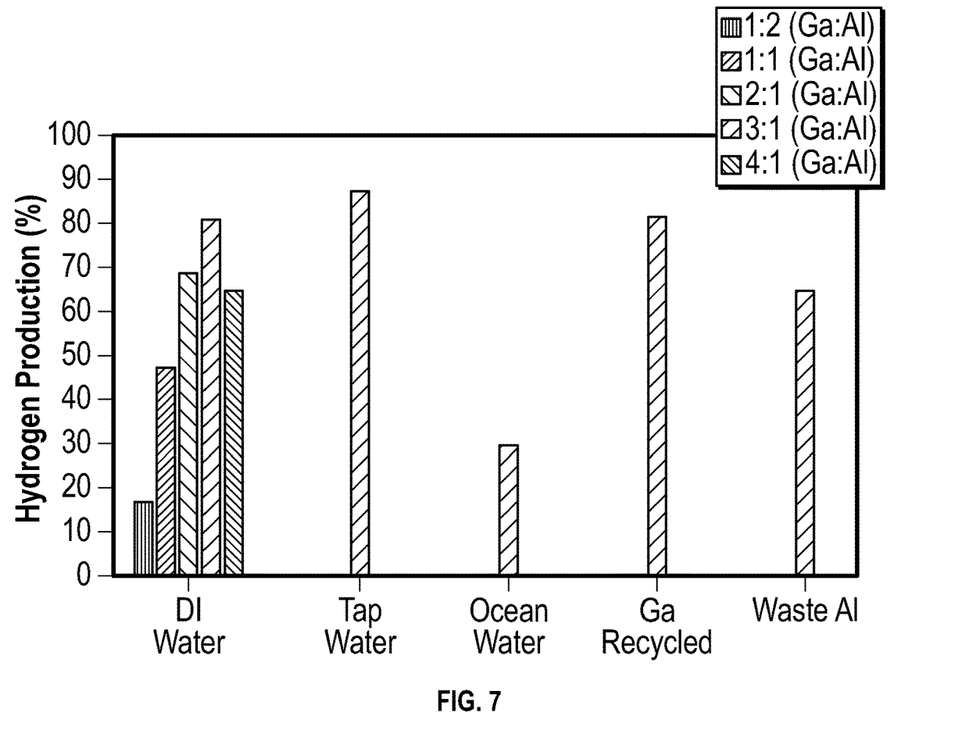
FIG. 7 is a bar graph of hydrogen production of Ga—Al alloy catalysts and different water types.

After using the Ga—Al liquid metal catalyst, Ga may be recovered and recycled to make additional Ga—Al liquid metal catalyst. Ga may be recovered from the alloy after the reaction by filtration and an aqueous rinse. Recovery of the gallium may be about 98% or above using this method. The recovered gallium was not distinguishably different from fresh gallium in its ability to produce hydrogen in the presence of aluminum as shown in FIG. 7.

Low eutectic melting point obviates the need for adding energy to the alloy to keep it in its liquid phase. Although it is envisioned that additional energy may be added to the liquid metal catalyst to maintain its liquid phase. In embodiments, the liquid metal catalyst may have a melting point from about 25° C. to about 35° C., in which case the catalyst may be heated above room temperature to maintain its liquid phase.

The liquid metal catalysts according to the present disclosure allow for hydrogen production on demand to avoid storage and transportation of hydrogen gas, which requires liquefaction of hydrogen gas. The method of forming the liquid metal catalyst also avoids using heat and other energy intensive procedures, such as grinding and/or ball milling. Instead, the liquid metal catalyst may be formed by folding and pressing the constituent metals to mix the metals.

The present disclosure also provides for hydrogenation of alkenes using Ga—Al alloy disclosed herein. Hydrogenation of this alkene previously required pressurized systems and/or extreme temperature. This reaction uses a metal catalyst under pressurized hydrogen and heat to induce the transformation. The Ga—Al alloy may be used to generate hydrogen under atmospheric pressure and room temperature. Any alkene, such as alkene 4-phenyl-1-buten-4-ol, may be used with a hydrogenation catalyst, which may be any suitable catalyst, such as a nickel-based catalyst, a platinum-based catalyst, a ruthenium-based catalyst, an iridium-based catalyst, and the like. Hydrogen may be generated ex situ by contacting Ga—Al alloy with a hydrogen generating compound, such as water, alcohol (e.g., methanol). Hydrogen may be transferred, e.g., via a cannula, into the reaction mixture. The alkene may be hydrogenated from about 30 minutes to about 2 hours, and in embodiments, may be about an hour.

The following Examples illustrate embodiments of the present disclosure. These Examples are intended to be illustrative only and are not intended to limit the scope of the present disclosure. Also, parts and percentages are by weight unless otherwise indicated. As used herein, "room temperature" or "ambient temperature" refers to a temperature from about 20° C. to about 25° C.

EXAMPLES

Example 1

Figure 1:
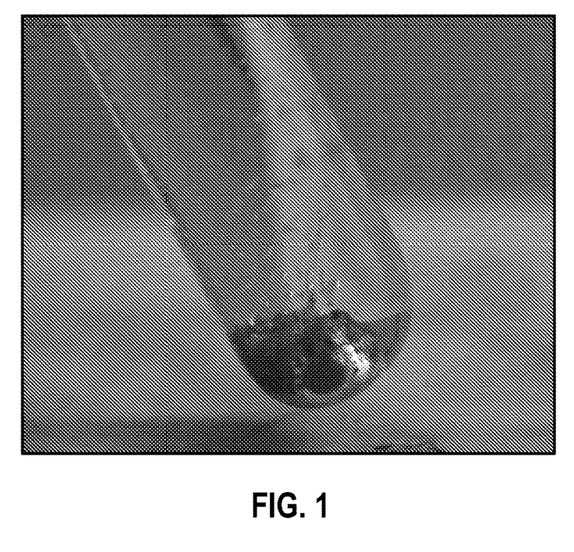
FIG. 1 is a photograph of a liquid metal catalyst submerged in water generating hydrogen gas according to an embodiment of the present disclosure.

This example describes preparation of binary and ternary liquid metal alloys. Aluminum was dissolved in gallium to form a liquid metal binary alloy to prepare samples 1-9. In samples 1-3, the liquid metal binary alloy was formed by heating aluminum and gallium at the stated ratios as noted in Table 1, below. Samples 4-9 were prepared by mixing aluminum and gallium. A droplet of each sample was submerged in water, which generated hydrogen gas, as shown in FIG. 1. Samples 1-4 and 6-9 were submerged in deionized water and sample 5 was submerged in ocean water. The reaction scheme for preparation of the aluminum/gallium liquid metal alloy and HER is shown below in Formulas (I) and (II), respectively:

$$Al + Ga \rightarrow Al/Ga \quad (I)$$

$$2Al/Ga + 3H_2O \rightarrow Al_2O_3 + 3H_2 + 2Ga \quad (II)$$

Figure 2:
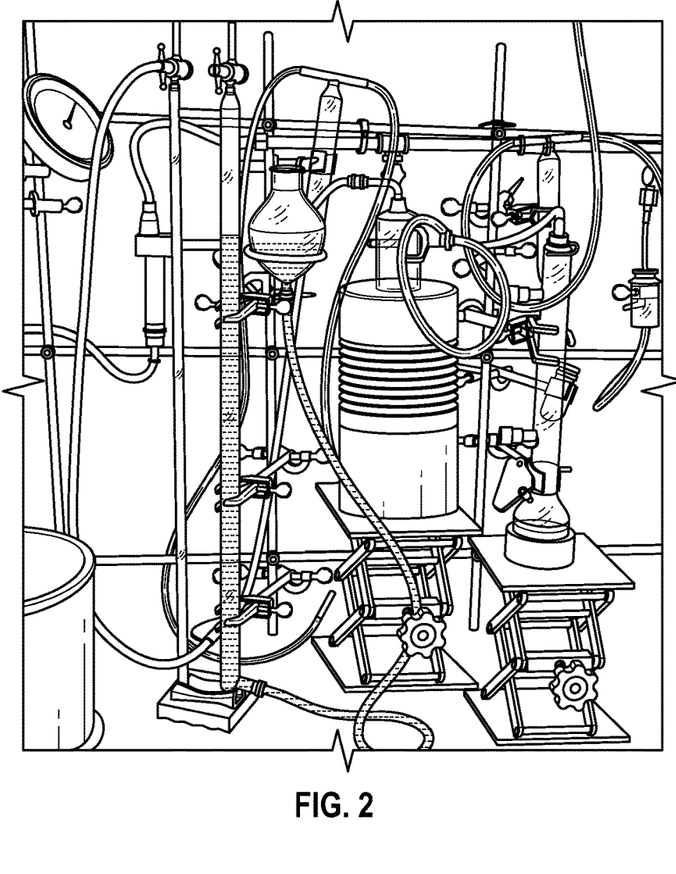
FIG. 2 is a photograph of a hydrogen meter for collecting hydrogen generated by reaction of the liquid metal catalyst with water of FIG. 1.

The amount of hydrogen generated by each of the samples 1-9 was measured and collected using a hydrogen meter shown in FIG. 2. Volumes of the collected hydrogen gas were recorded, and amount and yield were also calculated, which are also noted in Table 1. Sample 8 was prepared using recycled gallium, which was collected from prior use of the liquid metal catalysts. Sample 9 was prepared using 99.9999% pure gallium. It was observed that samples 8 and 9 had the highest yields of hydrogen gas out of all the samples 1-9.

TABLE 1

| Sample | Ratio | Method | Volume of Hydrogen | Amount (mmol) | Yield |
|---|---|---|---|---|---|
| 1 | (1:1, Ga:Al) | Heat gun | 17.6 mL | 0.70 | 23% |
| 2 | (2:1, Ga:Al) | Heat gun | 24.1 mL | 0.96 | 32% |
| 3 | (2:4, Ga:Al) | Heat Gun | 48.5 mL | 1.94 | 16.6% |
| 4 | (2:4, Ga:Al) | Mechanical mixing | 71.9 mL | 2.87 | 24% |
| 5 | (3:1, Ga:Al) ocean water | Mechanical mixing | 54 mL | 2.16 | 36% |
| 6 | (3:1, Ga:Al) | Mechanical mixing | 106 mL | 4.22 | 70% |
| 7 | (4:1, Ga:Al) | Mechanical mixing | 101 mL | 4.01 | 66% |
| 8 | (3:1, Ga:Al) recycled Ga | Mechanical mixing | 123.8 mL | 4.95 | 83% |
| 9 | (3:1, Ga:Al) ultrapure Ga | Mechanical mixing | 130.6 mL | 5.22 | 87% |

The aluminum oxide and gallium metal, which were byproducts of HER, were collected and characterized using PXRD. The plots of PXRD spectra of aluminum and gallium are shown in FIGS. 3 and 4, respectively.

Example 2

This example describes preparation of binary liquid Ga—Al metal alloys (in a 1:2, 1:1, 2:1, 3:1, 4:1, 6:1 atomic ratio [Ga:Al]) using aluminum foil.

On weigh paper, about 0.108 g/4 mmol of aluminum foil was shaped into a cup and into the center of the aluminum, about 0.837 g/12 mmol of gallium at room temperature was added to the aluminum to make a 3:1 Ga:Al alloy. The weigh paper was folded in fourths, thereby pressing the aluminum and gallium together through the weigh paper. Gallium was pressed and rubbed into the aluminum until the resulting alloy appeared homogenous and shiny in lustre. Once all the aluminum was dissolved into the gallium, the paper was folded in half and cooled, by pressing a dry ice pellet over the paper, solidifying the alloy. The Ga—Al alloy appeared dull grey after the alloy hardened. The alloy was peeled off the paper and re-weighed to calculate the weight. The alloy pieces were then stored under cyclohexane for further use. To store the alloy, the alloy pieces were re-melted and using a plastic syringe were withdrawn and then expelled into a bottle of cyclohexane. Ga—Al pellets stored under cyclohexane were tested periodically over several months of storage for their hydrogen production, with results comparable to freshly made alloys. The alloys can therefore be stored and used when needed without fear of reduction and premature hydrogen generation. Similar process was used to make 1:2, 1:1, 2:1, 3:1, 6:1 (Ga:Al) compositions by varying ratio of Ga to Al.

Example 3

This example describes preparation of a binary liquid Ga—Al metal alloy (6:1 Ga:Al) using aluminum from a soda can.

A top of a soda can was cut into pieces and was ground into a powder. About 0.108 g/4 mmol of the aluminum powder was placed on a piece of weigh paper and into the center of the aluminum about 1.68 g/24 mmol of gallium at room temperature was added to make 6:1 atomic ratio of Ga:Al alloy. The same process for combining the metals was followed as in Example 2 until a Ga—Al alloy was obtained, which was stored in cyclohexane.

Example 4

This example describes preparation of a binary liquid Ga—Al (3:1 atomic ratio Ga:Al) metal alloy using aluminum from a baking tray. The same process was followed to make the Ga—Al metal allows as in Example 2.

Example 5

This example describes preparation of a binary liquid Ga—Al (3:1 atomic ratio Ga:Al) metal alloy using aluminum from contaminated aluminum foil (previously used to as food wrap). The same process was followed to make the Ga—Al metal allows as in Example 2.

Example 6

This example describes preparation of a binary liquid Ga—Al (3:1 atomic ratio Ga:Al) metal alloy using recycled Ga. Ga was collected using a vacuum filtration apparatus and separated visually from the collected residue. The process for forming the Ga—Al was the same as the process of Example 2.

New commercial grade aluminum foil was initially used to optimize the alloy ratio, but expansion to waste aluminum in the form of baking trays and food wrappers demonstrated that hydrogen is efficiently generated regardless of the aluminum source. The top of a soda can was shown to produce about 80% of the theoretical amount of $H_2$ produced with fresh aluminum. The top of the can was used as opposed to the sides because the top contained the highest concentration of aluminum without any paint or polymer coating. When testing the soda can it was discovered that a higher ratio of gallium was used to dissolve the aluminum completely due to its greater thickness.

Example 7

Figure 5:
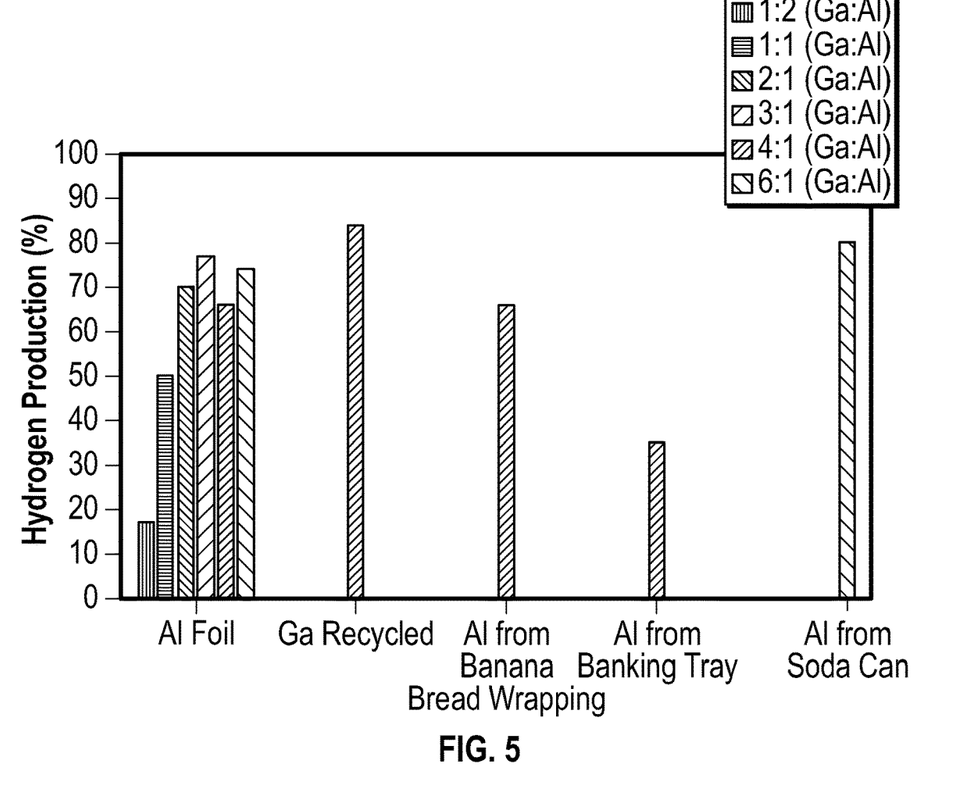
FIG. 5 is a bar graph of hydrogen production of gallium-aluminum (Ga—Al) alloy catalysts according to the present disclosure.

This example describes measuring HER using a gas burette of the hydrogen meter shown in FIG. 2. Hydrogen production of each of alloys of Examples 3-6 was tested using deionized water. A nugget of each of the alloys was placed in a round-bottom flask and melted using a magnetic stirrer warmed to about 60° C. About 10 mL of deionized water was added to the flask, causing $H_2$ gas to evolve immediately. By the controlled release of pressure in the closed system into a graduated buret, the volume of gas generated and was measured by water displacement. After approximately 15 minutes, the temperature of the displaced water and barometric pressure were also measured. The HER of each of the alloys is reproduced in the bar graph of FIG. 5.

Figure 6:
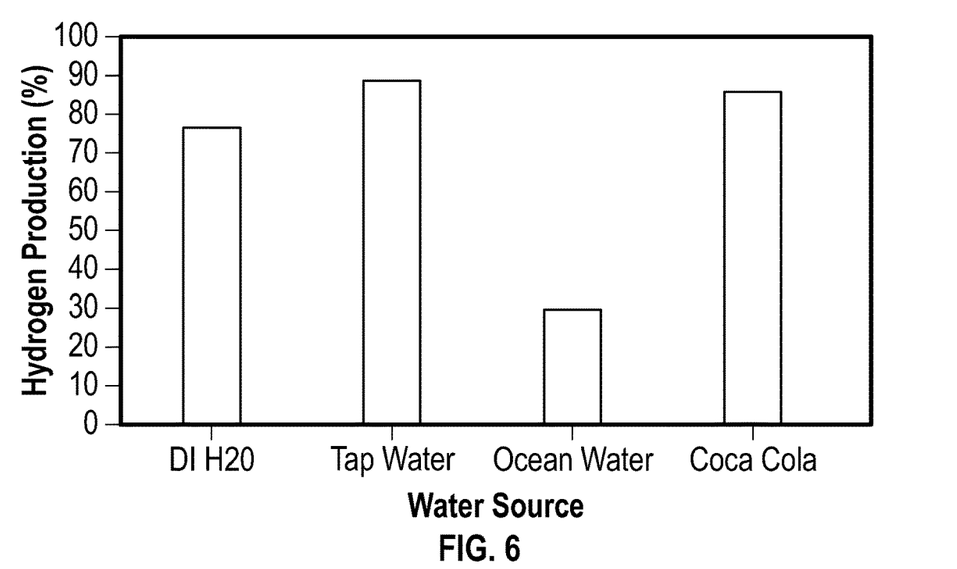
FIG. 6 is a bar graph of hydrogen production of a Ga—Al alloy catalyst with different water types.

In addition to deionized water, $H_2$ evolution was also measured using tap water, ocean water, and de-gassed COCA-COLA® (carbonated sweetened beverage) and 3:1 atomic ratio Ga—Al alloy of Example 2. The results of $H_2$ evolution of 3:1 atomic ratio Ga—Al with deionized water, tap water, ocean water, and de-gassed soda are shown in FIG. 6.

Besides deionized water, other water sources were shown to successfully generate hydrogen using 3:1 atomic ratio Ga—Al alloy. Tap water produced substantial amounts of hydrogen, similar to deionized water. Ocean water or simulated sea water (e.g., saline) produced approximately 30% of the theoretical amount of $H_2$ and about 40% of the amount produced using deionized water.

Visual comparison between the reaction the alloy with deionized water compared with ocean water showed a much less vigorous reaction for the latter. However, ocean water was still shown to be a viable hydrogen source. This yield demonstrated that it is possible to use a variety of water sources with this alloy to achieve excellent hydrogen production. Collected hydrogen gas was subjected to gas chromatography-mass spectrometry analysis, which confirmed that no detectable chlorine gas was formed, a pervasive problem that prevents the use of electrode-based water splitting, particularly in saltwater.

Example 8

This example describes analysis of the 3:1 atomic ratio Ga:Al alloy of Example 2.

Figure 8:
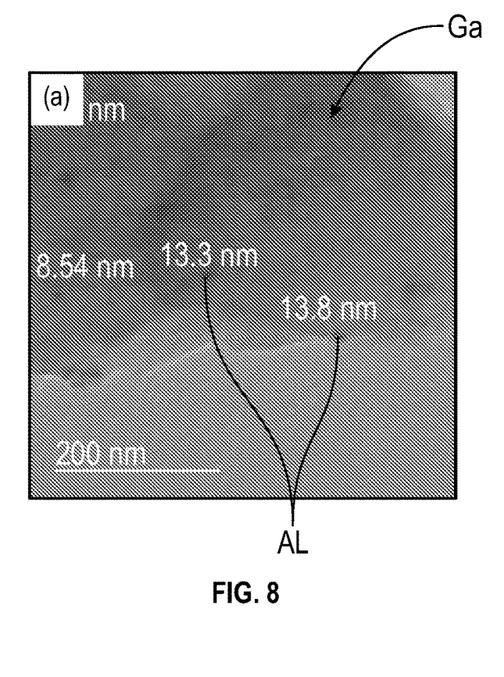
FIG. 8 is a transmission electron microscopy (TEM) image at 200 nm scale of Ga—Al according to the present disclosure.

The 3:1 atomic ratio Ga:Al alloy of Example 2 was analyzing using transmission electron microscopy (TEM). TEM of the 3:1 atom ratio Ga:Al alloy revealed nanoparticles of aluminum having a diameter from about 5 nm to 30 nm (FIG. 8). Both electron energy loss spectroscopy and selected area electron diffraction confirmed the dark areas are Al and the lighter areas in between Al nanoparticles are Ga. Furthermore, scanning electron microscopy with energy dispersive spectroscopy analysis showed a homogeneous distribution of Al particles in the Ga (FIG. 9).

Powder X-ray diffraction (PXRD) was performed on Ga:Al alloys of Example 2 (FIG. 10). Ga and Al references were calculated from single crystal X-ray structure from the American Mineralogist Crystal Structure Database (AM-CSD). Orthorhombic gallium (Cmca) has characteristic diffraction peaks at 30.3, 30.6, 45.4, 46.4, 57.6, 63.6, 76.3 and 77.0° (2θ). Cubic aluminum (Fm3m) has characteristic diffraction peaks at 38.5, 44.7, 65.1, and 75.3° (2θ). Utilizing in-plane PXRD, characteristic peaks of orthorhombic Ga and cubic Al are seen in all 6:1 to 1:4 Ga:Al mixtures. This suggests both aluminum and gallium retain their crystal structure after mixing and do not form a homogenous alloy.

Example 9

This example describes hydrogenation of alkene, i.e., 4-Phenyl-1-butene-4-ol, using hydrogen generated by reaction of 3:1 atomic ratio Ga—Al alloy of Example 2.

In a 100-mL round-bottom flask, about 1 g, 26.43 mmol of NaBH4 was suspended in about 24 mL of EtOH and 1.25 mL, and 2.5 mmol of 2M NaOH. The reaction mixture was filtered and set aside at about 25° C. In a separate 100-mL round-bottom flask, about 0.314 g, 1.25 mmol of nickel(II) acetate tetrahydrate was dissolved in about 12.5 mL EtOH. To the nickel solution, about 1.25 mL, 1.38 mmol of the $NaBH_4$ solution was added slowly via syringe to commence $H_2$, which results in $H_2$ evolution. Once the hydrogen evolution abates, the stirring was stopped and about 0.187 mL, 1.25 mmol of the alkene, 4-phenyl-1-butene-4-ol, was added to the reaction flask and a balloon was then connected to the reaction flask.

About 0.63 g (4 mmol of theoretical $H_2$) of 3:1 Ga—Al alloy of Example 2 was placed into a separate round-bottom flask and melted with a warm stir bar. The alloy containing flask was connected via cannula to the reaction flask containing the nickel catalyst and the alkene. With both flasks stirring, about 10 mL of deionized water was added to the alloy flask to generate hydrogen that is then led into the reaction flask. After approximately 15 min, the two flasks were disconnected, and a second flask containing about 0.787 g (5 mmol of theoretical $H_2$) of 3:1 Ga—Al alloy of Example 2 was attached and the same procedure as above was conducted to generate hydrogen gas. After the hydrogen had evolved, the reaction mixture was allowed to stir for about 1 h. The reaction mixture was then centrifuged, and the supernatant decanted. The solid catalyst was rinsed with about 2×10 mL of diethyl ether, centrifuged, and the supernatant decanted. The combined supernatants were then concentrated by rotary evaporation and the product, 1-phenyl-1-butanol, analyzed via $^1H$ and $^{13}C$ NMR. The same process was repeated using about 10 mL of methanol instead of deionized water and achieved the same result.

It will be appreciated that of the above-disclosed and other features and functions, or alternatives thereof, may be desirably combined into many other different systems or applications. Various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, or material.

What is claimed is:

1. A catalyst composition comprising gallium and aluminum at an atomic ratio from about 2:1 to about 5:1 of gallium to aluminum, wherein aluminum includes particles having an average size from about 5 nm to about 30 nm diameter dispersed in gallium.

2. The catalyst composition of claim 1, wherein the catalyst composition has a melting point from about 20° C. to about 25° C.

3. The catalyst composition of claim 1, wherein gallium and aluminum are present at an atomic ratio of from about 2.5:1 to about 4:1 of gallium to aluminum.

4. The catalyst composition of claim 3, wherein gallium and aluminum are present at an atomic ratio of from about 2.5:1 to about 3.5:1 of gallium to aluminum.

5. The catalyst composition of claim 1 provided as a pellet of at least 0.1 g, at least 1 g, at least 10 g, at least 100 g, or at least 1000 g in mass.

6. The catalyst composition of claim 5 where the pellet is stored under an alkane.

* * * * *